United States Patent [19]

Lanier

[11] Patent Number: 4,862,740
[45] Date of Patent: Sep. 5, 1989

[54] GLUE BOND TESTER

[75] Inventor: William G. Lanier, Marietta, Ga.

[73] Assignee: The Mead Corporation, Dayton, Ohio

[21] Appl. No.: 311,015

[22] Filed: Feb. 15, 1989

[51] Int. Cl.⁴ ............................................. G01N 19/04
[52] U.S. Cl. ..................... 73/150 A; 73/827
[58] Field of Search ............................ 73/150 A, 827

[56] References Cited

U.S. PATENT DOCUMENTS

| | | | |
|---|---|---|---|
| 3,129,586 | 4/1964 | Allen et al. | 73/150 R X |
| 3,396,578 | 8/1968 | Skundberg | 73/827 X |
| 4,027,529 | 6/1977 | Olsen | 73/827 |
| 4,080,825 | 3/1978 | Liebrenz et al. | 73/150 A |

OTHER PUBLICATIONS

Bulletin #250.1, W. C. Dillon & Company, PO Box 1501 Santa Rosa, CA 95402, 1986, "Electronic Force Gauge".

Primary Examiner—Daniel M. Yasich
Attorney, Agent, or Firm—Biebel, French & Nauman

[57] ABSTRACT

A glue bond testing apparatus for testing the glue bond at the end flaps of paperboard cartons, such as commonly used for packaging canned or bottled beverage products, is provided with a carton support which is adapted to receive an erected filled and glued carton and hold the same against movement. A gripper plate or clamp is secured to the carton end flap, the glue bond of which is to be tested. An electronic strain gauge is mounted on the apparatus with a force input rod connected to the clamp through a removable rigid connection. The electronic force gauge is slidably mounted on a pair of parallel rods for back and forth movement in a direction toward and away from the gripper plate. The carton support is arranged to support the carton to be tested at an angle to the direction of movement of the electronic force gauge so as to simulate the hand opening test of the flap. A single revolution cam operates with a cam follower to drive the force gauge on the guide rods away from the carton, thereby pulling the flap to be tested open with pivotal movement about the flap score line, breaking the glue bond and providing a direct indication of the force required. With continued revolution of the cam, return springs on the guide rods brings the test apparatus back to its start position. A releasable coupling is provided by which the clamp may be quickly and easily connected and removed from the force gauge following the test.

12 Claims, 5 Drawing Sheets

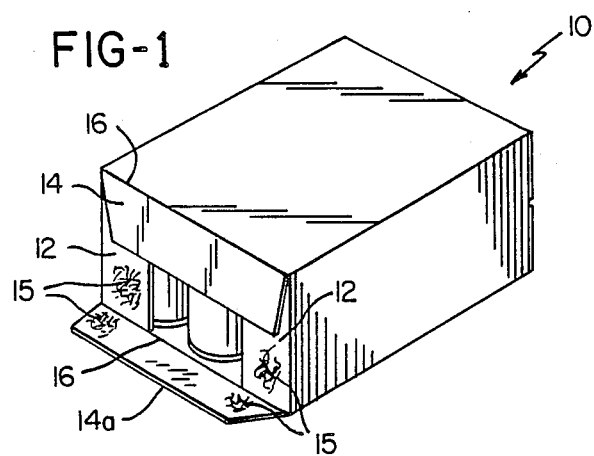
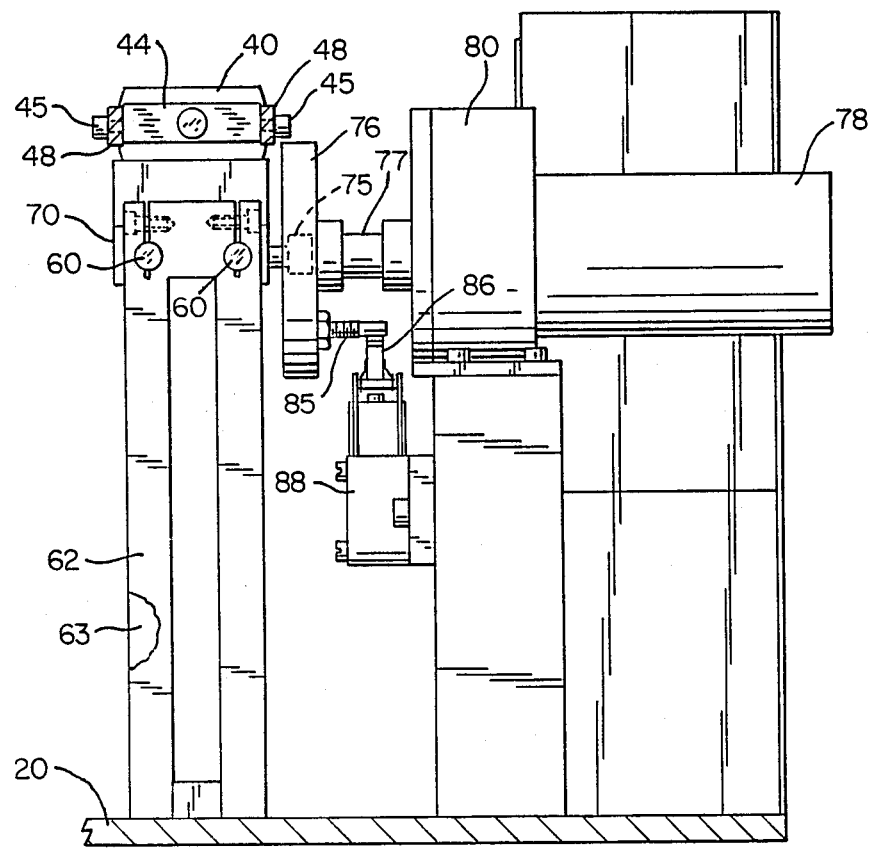

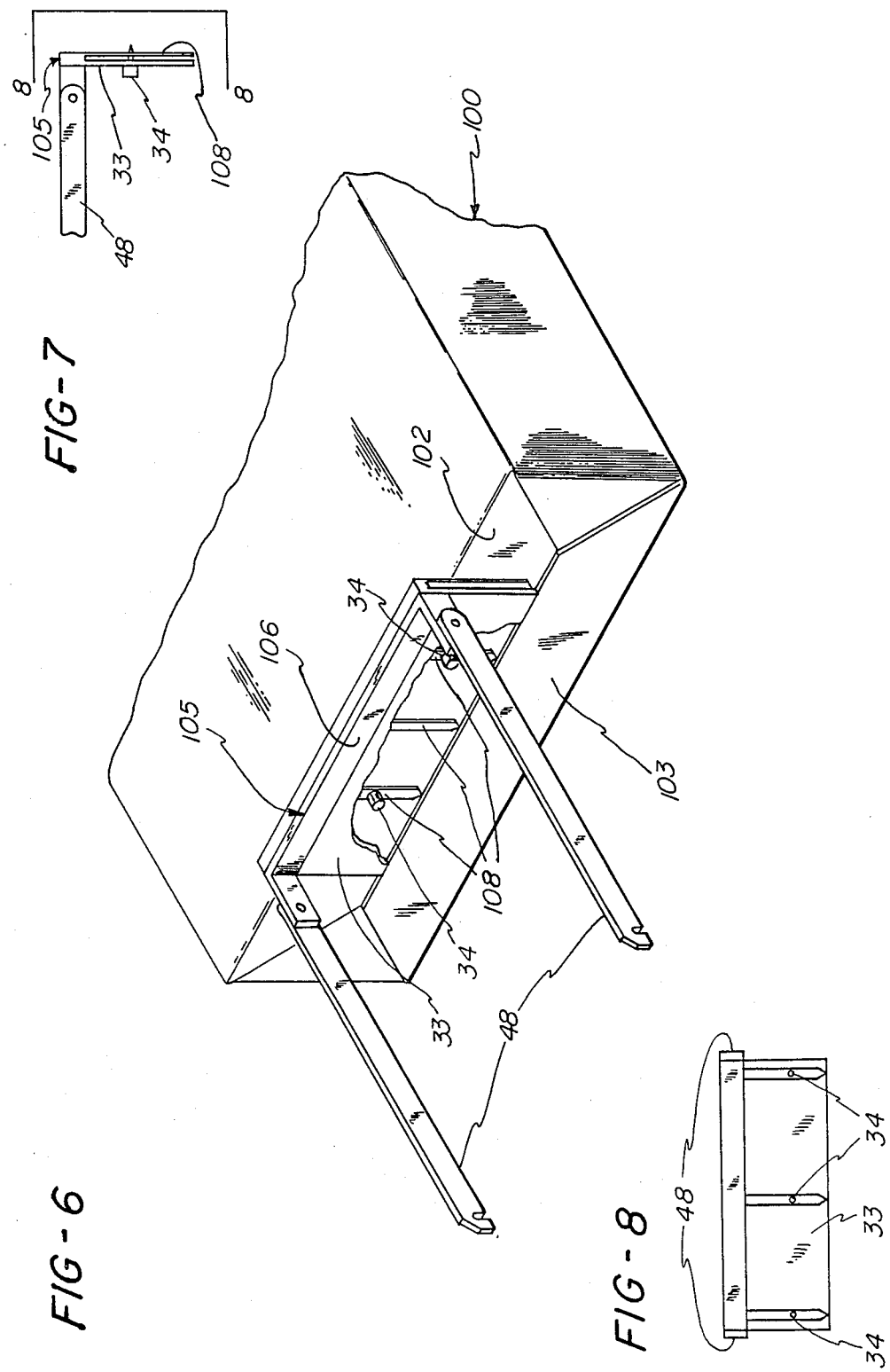

GLUE BOND TESTER

BACKGROUND OF THE INVENTION

This invention relates to glue bond testing, and more particularly to apparatus for testing the integrity of the glue bond of a flap of a paperboard carton or container.

In the packaging industry and particularly in the business of automatic filling and packaging of canned or bottled soft drink, beer and the like, there is a need to be able to check the integrity of the glue bond of the paper end flaps of paperboard cartons, and particularly the cartons which contain canned and bottled beverages. Typically, the cartons which contain such beverages are formed of coated, unbleached board stock, and the coating is typically a clay coating to provide a superior surface for printing. This surface must also provide a satisfactory glue bonding cite, compatible with on-line gluing operations forming a part of the filling and packaging of such products.

Typically, the integrity of the glue joint formed between the end flaps is tested by hand. This is done by taking a filled carton off the line and manually pulling one of the end flaps away, while subjectively noting how difficult it is to pull the flap. Also, the interface between the previously joined flaps is viewed to determine the extent to which fiber tear has been produced, that is, the extent to which the board itself has been caused to separate, rather than merely part across the glue interface. Those in industry who customarily practice testing by manually opening a carton have commonly viewed splitting of the coating, as distinguished from fiber tear, as an indication of a poor internal bond strength.

Recent investigations have concluded that the extent to which fiber tear is exposed is not necessarily an indication of the integrity or actual strength of the glue bond at the end flaps of a paperboard carton. Thus, depending on the surface characteristic of the board and other characteristics of the fiber and the glue, a glue bond separation along or through the glue interface may not be an indication of an inadequate glue bond.

The manual test of pulling a carton open by hand, presently used by many of the carton converters and product manufacturers, involves a substantial subjective element, making this evaluation difficult to interpret, and usually not repeatable. Prior art glue bond testers, to eliminate the subjective element, typically involve the testing of a specially prepared laboratory glue bond joints in a laboratory instrument, to provide an indication of the joint which can be expected in actual use. Thus, the U.S. patents of Skundberg, 3,396,578 issused Aug. 13, 1968 and Liebrenz et al, 4,080,825 issued Mar. 28, 1978 exemplify glue bond testers in which specially prepared strips are formed, the bonds of which are tested by the apparatus shown in those patents. These instruments are not adapted to the testing of production cartons taken off line for quality control inspection.

There is accordingly a need for apparatus which provides a quantitative evaluation of the opening force of a glued or bonded carton flap, and a need particularly for such an instrument which permits standardization of testing parameters and techniques, so that direct comparisons can be made between tests.

SUMMARY OF THE INVENTION

This invention provides a tester or apparatus for measuring the glue bond strength of a carton flap, and employs an electronic force gauge coupled to mechanical apparatus which simulates the manual tearing operation, while eliminating the subjective variables.

The glue bond tester of this invention accordingly provides a support for holding and retaining a filled and glued carton to be tested. The retention of a carton in a support, including solid structure to support the carton, is important to prevent buckling of the carton material during the opening operation.

A flap gripping device or clamp positively engages one of the end flaps of the carton, the bond of which is to be tested. The apparatus includes a releasable pull connection between the flap gripping device or clamp, on the one hand, and the force input shaft of the electronic force gauge on the other hand. Preferably, the releasable pull connection consists of rigid pull rods which can be quickly and easily connected and disengaged from one or the other ends, in the assembly of the flap clamping device to the carton, while the carton is retained in the support frame, to couple and uncouple the clamping device to the force gauge.

Preferably, the axis of the carton itself is held at an angle, such as 45°, to direction of pull to simulate the direction that force would normally be applied when gripping a flap by hand and pulling it open about the score line. The carton and support, on the one hand, and the electronic force gauge on the other hand, are mounted for relative movement in such a manner that the pull connection between the force gauge input shaft and the carton flap clamp causes the carton flap under test to be pulled away from the carton and bent about the score line.

Preferably, the force gauge itself is mounted on a slide for movement back and forth in a direction which is generally parallel to the actuating direction of the gauge and toward and away from carton. This mounting, in the preferred embodiment, includes a pair of guide rods and a gauge support slidably mounted on the rods. Springs on the rods urge the force gauge in a home or rest position, and a single revolution cam is employed with a cam follower coupled to the gauge support for causing the gauge to move on the rods in a direction away from the carton, thereby causing the flap under test to be separated from the carton, followed by the return to the home position.

Preferably, the rate of turning of the cam may be adjusted or selected to simulate the approximate rate by which an end flap has been commonly opened by hand testing. The force gauge can be programmed to store in memory the maximum separating force. Additionally, the output of the force gauge may be connected to a plotter to provide a curve of the applied forces.

In addition to providing a direct and reliable indication of the strength of a glue bond, the apparatus of this invention also provides a tool for evaluating the filling-line performance, considering such variables as glue temperature, compression, materials, glue placement, etc., all as judged by carton bond integrity.

A principal object of the invention is the provision of a tester for testing the glue bond integrity of a carton flap and to provide a consistent and reliable indication of the forces which are required to separate the glue bond, in a completed carton.

A further object of the invention is to provide versatile apparatus as outlined above which can be used to test a wide variety of cartons, which is easy to use, and which is easy to assembly and attach to the carton flap.

BRIEF DESCRIPTION OF ACCOMPANYING DRAWINGS

FIG. 1 is a perspective view of a typical beverage can paperboard carton with glued end flaps, the glue bond integrity of which can be tested by the apparatus of this invention;

FIG. 3 is a vertical section through the tester looking generally along the line 3—3 of FIG. 2;

FIG. 6 is a perspective view of a modified carton flap gripper plate of this invention.

FIG. 7 is a side elevational view of the modified gripper plate; and

FIG. 8 is an end elevation looking along the line 8—8 of FIG. 7.

DESCRIPTION OF PREFERRED EMBODIMENTS

Figure 2:
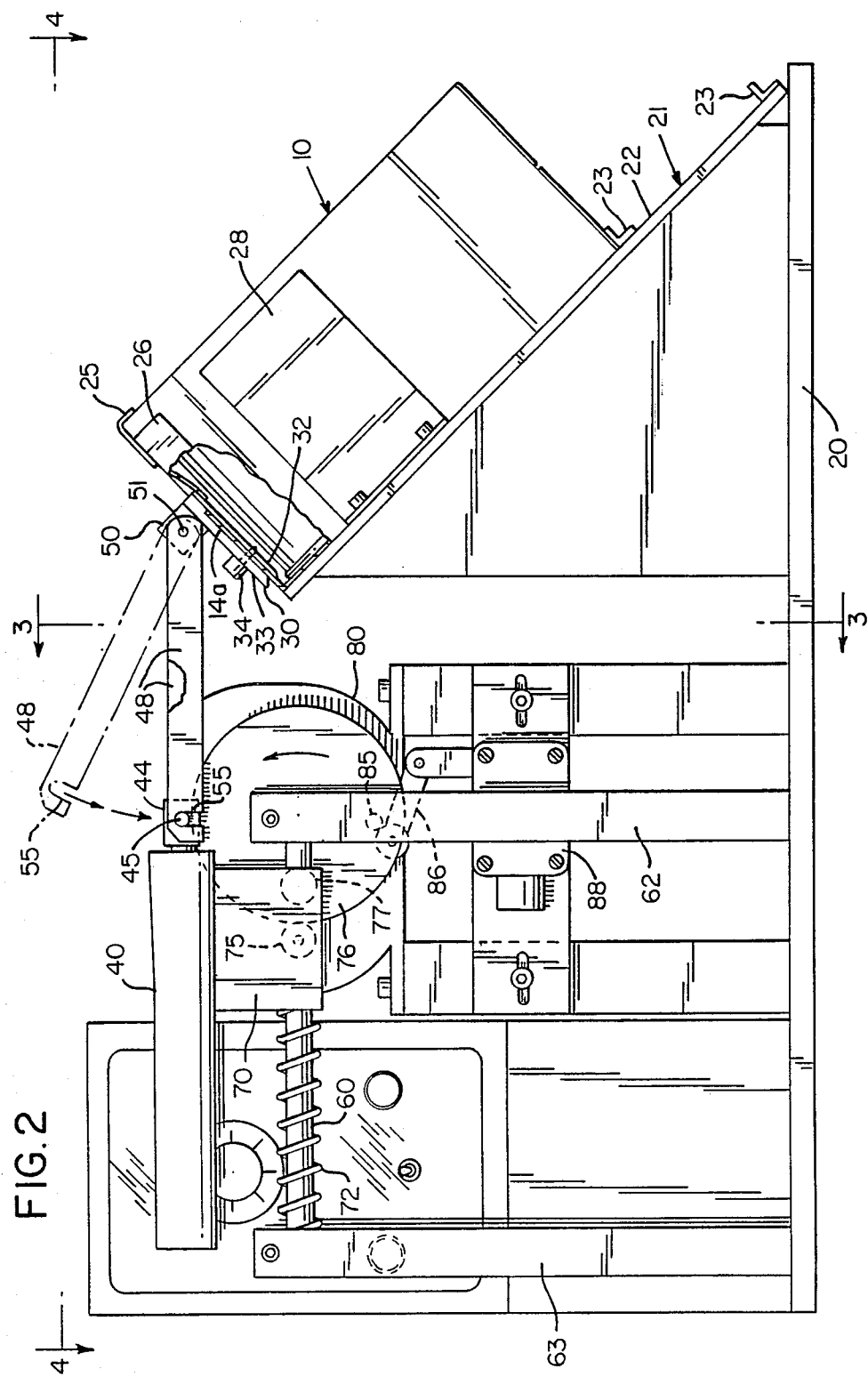
FIG. 2 is a side elevation of the glue bond tester of this invention.

Referring to the figures of the drawing, which illustrate preferred embodiments of the invention, a typical paperboard carton for holding twelve cans of twelve ounce beverage, such as beer, is illustrated at 10 in FIG. 1. The carton 10 includes, at each end, a pair of inwardly turned side flaps 12, and a pair of top and bottom end flaps 14. The inside surface of the flaps 14 and the outside surfaces of the side flaps 12 provide glue bond surfaces 15 to which glue is applied and by which the end flaps 14 are normally closed. In the case of the carton 10, the end flaps 14 do not overlap but are separated by a small slot of approximately ⅛. Each of the flaps 14 is connected to its respective top or bottom surface of the carton by a score line 16. In the manual testing of the carton, one of the flaps, such as the flap 14a of FIG. 1, is pulled down by hand to the position shown, and the physical condition of the glue bond and the carton fiber at the regions 15 are observed for condition and for fiber separation.

In the present invention, much of the guess work and subjective judgment as to the condition or integrity of a glue bond is eliminated. Referring to the side elevation of the apparatus, as shown in FIG. 2, a rigid base 20 carries at one end a carton support or holder 21 for receiving a carton to be tested, such as the carton 10 in FIG. 1. For the purpose, the support 21 is provided with an inclined floor 22 against which one flat surface, such as the carton bottom, may rest. Angle braces 23 support the carton at the bottom and prevent it from sliding down the surface of the inclined floor 22. One or more pairs of braces 23 may be employed to accommodate cartons of varying lengths. Means for fixing the braces 23 in alternate positions on floor 22 may be provided to further accommodate varying carton sizes.

Figure 4:
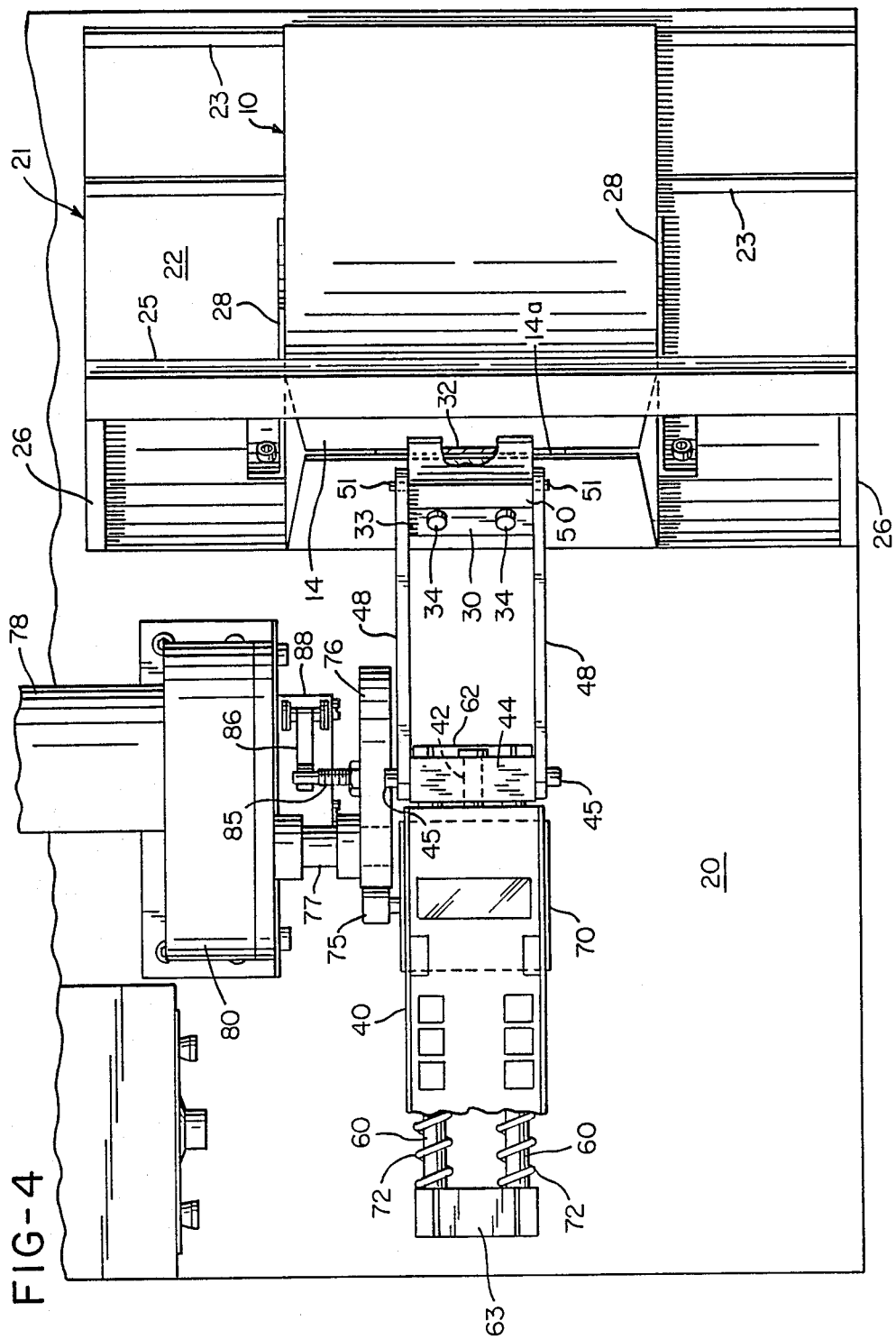
FIG. 4 is a plan view, partially broken away, looking generally along the view line 4—4 of FIG. 2.

The support 21 further includes an end frame at its upper end. The upper end frame includes a generally L-shaped cross member 25 which engages the top edge of the carton, supported on the frame by a pair of side portions 26. As shown in FIG. 4, the side portions 26 are joined to the base or floor 22, at the upper inclined end of the floor. The cross frame member 25 is thus held rigidly in place to provide a firm support for the top of the carton 10. Also, a pair of side plates 28, as best shown in FIG. 4, may be employed to provide support for the carton sides and may be adjustably mounted on the floor 22 to accommodate the particular width of the carton. The space between the cross member 25 and the side portions 26 is open at the front to provide access to flap 14a, as shown in FIG. 1.

The glue bond test apparatus includes a gripper or clamp which is generally illustrated at 30 in FIG. 2. The clamp 30 has a width which substantially equals the space between the side flaps 12, and is provided with a relatively thin inside leg portion 32 which is proportioned to be received through the ⅛" slot and dropped down over the back of the flap 14a. The clamp also includes a front leg portion or plate 33 spaced from the back portion 32 defining a narrow slot therebetween which conveniently receives the flap. A pair of locking pins 34 may be pushed through access openings in the front and back clamping legs and through the flap in order to pin the flap in place, to prevent the clamp 30 from being pulled off of the flap during the test. In this manner, the clamp or gripper plate 30 may be readily attached to one of the flaps, such as the flap 14a of FIG. 1, for the pull test.

The invention further includes an electronic force gauge 40 which has a force input rod or shaft 42 (FIG. 4) extending from the forward end thereof. While any suitable electronic strain gauge or force gauge may be used with an operable working range from between about one and twenty pounds, for typical cartons, a preferred commercially available electronic force gauge is that as provided by W. C. Dillon & Co., Inc., 2320 Airport Boulevard, Santa Rosa, CA 95402, described in Bulletin #250.1 dated 1986. This force gauge is preferred in that it provides instant zero reset and tare adjustment, permits instant conversion between pounds, kilograms, and Newtons, and may be provided with a serial RS232C port for data output.

The electronic force gauge 40 is provided, on its input shaft 42, with a crosshead 44 terminating in a pair of transversely or outwardly extending pins 45. Means for coupling the force gauge to the clamp 30 includes a pair of rigid identical pull rods 48. The one end of each of the rods 48 is pivotally coupled to the sides of a bracket 50 forming an integral part of the clamp 30, for pivotal movement about a pin 51. The remote ends of the rods 48 are notched at 55 to drop over the pins 45 and couple the clamp 30 to the force gauge 40. The full line position of the pull rods 48 show the condition when the force gauge is coupled to the clamp 30 in the home or start position of the apparatus. The broken line position in FIG. 2 of the rods 48 show the position prior to coupling the clamp 30 to the force gauge 40, and therefore prior to pull test. Thus, the rods 48 form a releasable coupler by means of which the clamp or gripper plate 30 is connected to the input rod of the gauge 40.

Means for mounting the gauge 40 for relative movement toward and away from the carton support means, including the support 21 and the frame 25, includes a pair of parallel spaced-apart slide rods 60 as shown in FIGS. 2 and 4. The forward ends of the rods 60 are supported on the base 20 by forward vertical support posts 62 (FIG. 3) while the rear ends of the rods 60 are supported on similar rear support posts 63 (FIG. 2).

A slide block 70 is mounted for sliding movement on the rods 60 and supports the gauge 40 on an upper surface thereof. A pair of compression springs 72 between the block 70 and the top of the posts 63 urge the support block 70 toward the forward or home position as shown in FIG. 2. The springs 72 also assure the maintenance of the position of a cam follower 75 against a single revolution drive cam 76. The cam follower 75, as shown in FIG. 4, is offset from the block 70, but is otherwise rigidly attached to the block so that movement is imparted by the cam 76 directly to the follower 75 and from the follower 75 to the block 70.

The drive cam 76 is shown in the drawings as a simple circular cam mounted on an offset axis, on the output shaft 77 of a gear reduction motor 78. While the circular cam has the advantage of simplicity and low cost, it may be desirable to employ an oblong cam to provide a constant velocity to the rate of pull on the flap 14a. Preferably the motor 78 is controlled by a conventional, commercially available controller 80, permitting regulation of the speed of revolution of the cam 76.

Figure 5:
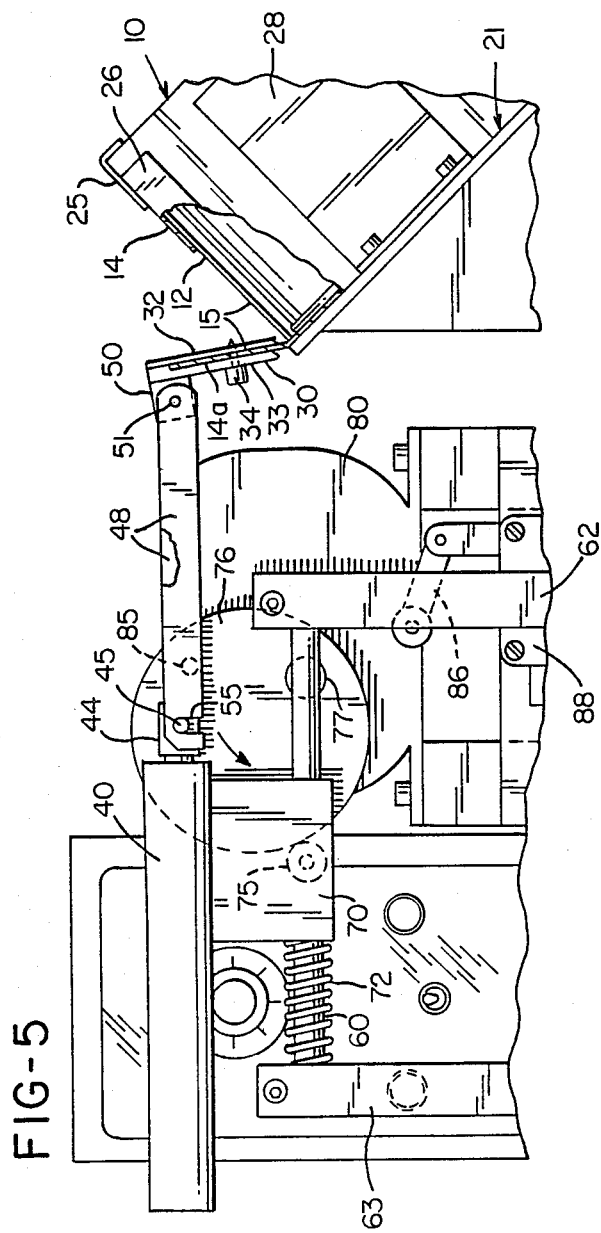
FIG. 5 is a view of a portion of the apparatus of FIG. 2 showing the parts in a moved position.

The offset of the cam 76, transmitted to the follower 75, is sufficient to move the force gauge 40 in translation, on the parallel guide rods 60, so as to pull the flap 14a fully away from its closure position on the carton, as illustrated by the moved position in FIG. 5. The continued revolution of the cam permits the block 70 to be carried forwardly on the guide rods by the compression springs 72 substantially back to the start position as shown in FIG. 2, with the full revolution of the cam. A projecting pin 85, mounted on an inside surface of the cam (FIG. 4) contacts the feeler 86 of a limit switch 88 to define a single cam revolution.

The operation of the invention is largely self-evident from the foregoing description. The carton 10 to be tested is placed on the sloping support 21 with its upper front edge against the cross member 25, between the frame side plates 28. The rear edge of the carton is supported on one of the rear stops 23. Preferably, the angle of the frame floor 22 is about 450 to the axis of the rod 60, to simulate a hand-opening operation, as previously described.

The clamp 30 is attached by sliding in place, as shown in FIG. 2, and the pins 34 inserted. In this condition, the back flange is received on the back side of the end flap 14a in the open space between the side flaps 12. The pair of rods 48 are then attached by dropping the notches 55 over the pins 45, as illustrated in FIG. 2 by the movement of the rods from the broken line position to the full line position.

The rear reduction motor 78 is started to drive the cam 76 in a single revolution, with the follower 75 carrying the block 70 and force gauge 40 with it, to the left as viewed in FIG. 2, to pull through the rods 48 and separate the flap 14a from the carton. This condition is shown in FIG. 5 with the flap separated from the glue bond regions 15 and bent about the score line 16. The maximum pulling force is recorded on the gauge 40, while the cam 76 continues its revolution to bring the parts back to the home position shown in FIG. 2. At this point, the value shown on the gauge may be manually or electronically recorded, and the rods 48 lifted off of the cross pins 45 to release the clamp from the gauge.

From time to time it may also be necessary or desirable to test the glue bond of the end flap of paperboard cartons in which the end flaps are overlapped. Such a carton is illustrated diagrammatically in FIG. 6 at 100 with overlapping end flaps 102 and 103. A modified form of end clamp is illustrated at 105, in which a plurality of spaced-apart and downwardly extending blades 108 take the place of the back portion 32 of the clamp 30. In other respects, the modified clamp member 105 will be substantially identical to the clamp member or gripper plate 30, and will have a front leg portion or plate 33 defining a space with the blades 108 to receive the lower flap 103 therebetween. Locking pins 34 extend through the back plate and intercept one of the blades 108, for pinning and locking the flap 103 in place. While three blades are shown, it is obvious that a fewer or greater number may be employed, as required.

The blades 108 are thin and are proportioned to be pressed between the flaps by inserting the same behind the outer flap 103 and in front of the inner flap 102 to lock the pull clamp 105 behind the outer flap.

It is also within the scope of this invention to provide a vacuum cup gripper in place of the clamp or gripper 30 or 105, which could be particularly useful in forming a non-destructive connection to a carton end flap, such as an overlapping flap of the kind shown in FIG. 6. It is therefore seen that this invention provides a highly versatile and easy-to-operate glue bond tester for providing consistent and accurate information as to the integrity of the glue bond in the flaps of paperboard cartons.

It will be recognized that in performing a test described herein, the specific value per se obtained from the gauge 40 is not important. Rather, what is important is that each test be performed in a consistent and repeatable manner. It is believed that the comparison of test results for various cartons will be the meaningful information.

While the invention herein has been described particularly in connection with a glue tester for testing the glue bond on completed paperboard cartons, such as may be pulled off of a filling line, it should be understood that the invention also has utility in the testing of glue bonds on carton blanks. In this context, the glue bond tester of this invention is useful in determining the integrity of glue bonds which will be formed at various locations in a completed carton, using various kinds of papers and glue materials.

While the forms of apparatus herein described constitute preferred embodiments of this invention, it is to be understood that the invention is not limited to these precise forms of apparatus, and that changes may be made therein without departing from the scope of the invention which is defined in the appended claims.

What is claimed is:

1. A glue tester for testing the glue bond at the ends flaps of a paperboard carton, comprising:
    a carton support adapted to receive a carton body and hold the same against movement;
    a gripper plate adapted to be secured to a carton end flap the glue bond of which is to be tested;
    an electronic strain gauge having a force input rod at an end thereof;
    operator means connecting said gauge at said rod to said plate including:
    means slidably supporting said gauge for back and forth movement in a direction generally parallel to said gauge rod and generally toward and away from said gripper plate,
    drive means including a single revolution cam and controllable to cause said cam to revolve on command,
    a cam follower,
    means coupling said cam follower to said to said gauge support means for causing said gauge to move on said support means in a direction away from said plate, resilient means urging said gauge in a direction toward said plate, and releasable coupling means connecting said plate to said gauge input rod, whereby operation of said drive means causes said cam to drive said follower and retract said gauge and connected plate breaking said glue bond.

2. The tester of claim 1 in which said gripper plate has a first portion insertable behind said flap and a second portion positioned in front of said flap defining a flap-receiving slot therebetween.

3. The tester of claim 2 in which said coupling means includes a transverse cross head connected to said rod, and a pair of parallel, spaced apart links removably coupling said cross head to said plate first portion.

4. The tester of claim 1 in which said carton support has a an end frame adapted to engage said carton at said flap end while leaving said end flap free, and means on said support positioning the body of said carton at an approximate 45 degree angle to said generally parallel direction to simulate the direction of pull if said flap were pulled by hand from said carton.

5. The tester of claim 1 in which said gripper plate includes thin blade means adapted to be inserted by pressing behind said flap for gripping said flap.

6. The tester of claim 1 in which said means slidably supporting said gauge includes a pair of parallel slide rods, block means mounted for sliding movement on said rods, and means mounting said gauge on said block means.

7. The tester of claim 6 in which said resilient means includes springs threaded on said rods and in engagement with said block.

8. A glue bond tester for measuring the strength of the glue bond of a paperboard carton end flap to the side flaps, comprising:

support means for holding a carton to be tested;
clamp means adapted to engage said end flap,
an electronic force gauge having a force input shaft;
releasable coupling means directly connecting said gauge at said input shaft to said clamp means;
slide means mounting said force gauge for relative movement toward and away from said carton support means;
a single revolution drive cam;
cam follower means in engagement with said cam and connected to cause relative sliding movement between said force gauge and said support means upon the rotation of said cam;
and drive means for causing said cam to rotate in a revolution for said relative movement between said force gauge and said support means with separation of said end flap by pull through said force input shaft and said pull means.

9. The tester of claim 8 in which said releasable coupling means includes a pair of rigid rods each having one of the ends thereof pivotally attached to said clamp means and having the other ends thereof pivotally attached to said force gauge at said gauge input shaft.

10. The tester of claim 9 further comprising a cross head mounted on said force tester input shaft, said cross head terminating in a pair of mutually outwardly-extending pins, and said other ends of said rods being formed with notches adapted to be received over said pins for releasably and pivotally coupling said rods to said cross head.

11. The tester of claim 9 in which said clamp means is adapted to be received over said end flap in the spaced between the carton side flaps, and includes an inside leg proportioned to be received behind said end flap and between said side flaps and an outside leg opposed to said inside leg defining a flap-receiving space therebetween, and pin means extending through said legs and through said space therebetween for impaling said end flap and retaining the same during said separation thereof from said side flaps.

12. The tester of claim 9 in which said clamp means includes a cross member, means on said cross member pivotally connected to said coupling means, and a plurality of spaced apart blades formed on said cross member and adapted to be inserted behind said end flap for gripping said end flap.

* * * * *